United States Patent [19]

Heider et al.

[11] Patent Number: 5,710,331
[45] Date of Patent: Jan. 20, 1998

[54] PREPARATION OF N-ALKENYL CARBOXAMIDES

[75] Inventors: Marc Heider, Neustadt; Thomas Rühl, Frankenthal; Jochem Henkelmann, Mannheim, all of Germany

[73] Assignee: BASF Aktiengesellschaft, Ludwigshafen, Germany

[21] Appl. No.: 548,724

[22] Filed: Oct. 26, 1995

[30] Foreign Application Priority Data

Oct. 27, 1994 [DE] Germany .................... 44 38 366.5

[51] Int. Cl.$^6$ .................... C07C 231/08; C07C 233/05
[52] U.S. Cl. .................... 564/215; 564/182; 564/183; 564/184; 564/189; 564/190; 564/192; 564/217; 564/218
[58] Field of Search .................... 564/182, 183, 564/184, 189, 190, 192, 215, 217, 218

[56] References Cited

U.S. PATENT DOCUMENTS

| | | | |
|---|---|---|---|
| 4,490,557 | 12/1984 | Dawson et al. | 564/159 |
| 4,567,300 | 1/1986 | Murao et al. | 564/215 |
| 4,670,531 | 6/1987 | Eckberg | 528/15 |
| 4,670,591 | 6/1987 | Oftring et al. | 564/224 |
| 4,968,841 | 11/1990 | Listemann et al. | 564/159 |

FOREIGN PATENT DOCUMENTS

| | | |
|---|---|---|
| 34 43 463 | 11/1984 | Germany . |
| 36 22 013 | 7/1986 | Germany . |

OTHER PUBLICATIONS

*Chem. Abst.*, vol. 120, No. 4, Jan. 24, 1994, Abstract No. 31326m, Sawayama et al., "A new synthetic procedure for N-vinylformamide . . . ".
*Patent Abst. of Japan*, vol. 11, No. 259 (C–441), 2706, Aug. 21, 1987 (English equivalent of JP-A 62 059248, Mar. 14, 1987).
*Das Papier*, 46/10A, 1992, pp. V38–45.
*Appl. Catal.*, 78, 1991, p. 65.
Graham et. al., J. Med. Chem., 30, 1074–1090, 1987.

*Primary Examiner*—Shailendra Kumar
*Attorney, Agent, or Firm*—Keil & Weinkauf

[57] ABSTRACT

Preparation of N-alkenyl carboxamides of the general formula I

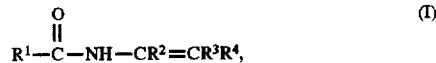

(I)

in which the radicals $R^1$ to $R^4$ independently stand for hydrogen or for aliphatic, cycloaliphatic, or aromatic radicals, which optionally carry inert substituents, wherein an amide of the general formula II

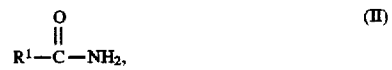

(II)

in which the radical $R^1$ has the above meaning, and a carbonyl compound of the general formula III

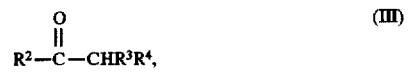

(III)

in which the radicals $R^2$ to $R^4$ have the above meanings, are caused to react in the presence of a base, said reaction being either a) carried out in the presence of a carboxylic acid derivative of the general formula IV

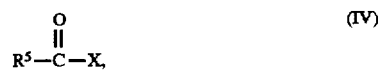

(IV)

in which the radical $R^5$ stands for hydrogen or an alkyl or aryl group and X is a halogen, alkoxy, or carboxylalkyl radical, or b) continued in the presence of a carboxylic acid derivative of the formula IV, and the amide of the formula I is isolated.

6 Claims, No Drawings

PREPARATION OF N-ALKENYL CARBOXAMIDES

The present invention relates to a novel process for the preparation of N-alkenyl carboxamides of the general formula I $$R^1-\overset{O}{\overset{\|}{C}}-NH-CR^2=CR^3R^4, \qquad (I)$$

in which the radicals $P^1$ to $R^4$ independently stand for hydrogen or for aliphatic, cycloaliphatic, or aromatic radicals, which optionally carry inert substituents.

The end products of the formula I are desirable intermediates. N-alkenyl carboxamides can be polymerized in known manner and then be converted to the corresponding poly(vinyl amine)s by hydrolysis. These polymers, particularly poly(vinyl formamine), serve, for example, for the preparation of dyes, pharmaceutical products, flocculating agents, and viscosity regulators in the paper industry (Linhard et al, *Das Papier* 46/10A (1992), pp. V 38–45).

N-vinyl formamide can be prepared from ethylidene formamide by pyrolytic elimination at ca 300°–400° C. Ethylidene formamide can be prepared in the presence of acid catalysts, for example, by effecting mercury catalysis in an acid solution from formamide and vinyl acetate (DE-A 4,036,097) or from formamide and acetaldehyde (U.S. Pat. No. 4,490,557).

Other synthesis routes involve intermediates such as N-acetylethyl formamide (G. Parris, *App. Catal.*, 78 (1991) 65, N-alkoxyethyl formamide (DE-A 3,622,01 3, DE-A 3,520,829, U.S. Pat. No. 4,670,531 ), N-hydroxyethyl formamide (DE-A 3,500,773) and N-cyanoethyl formamide (DE-A 3,443,463). These compounds eliminate acetic acid, alcohols, water, and hydrocyanic acid respectively at relatively high temperatures ranging from ca 300° to 400° C.

The above synthesis processes comprise two stages and require a thermal elimination step. They are thus technically relatively elaborate and lead to inadequate overall yields due to losses of desired product at the high temperatures of reaction required. Furthermore, this method of synthesis is restricted to vaporizable intermediates so that difficultly volatile end products cannot be prepared. It was thus the object of the present invention to provide a process which avoids the aforementioned drawbacks of known processes.

Accordingly, we have found a process for the preparation of N-alkenyl carboxamides of the formula I, wherein an amide of the general formula $$R^1-\overset{O}{\overset{\|}{C}}-NH_2, \qquad (II)$$

in which the radical $R^1$ has the above meaning, and a carbonyl compound of the general formula III $$R^2-\overset{O}{\overset{\|}{C}}-CHR^3R^4, \qquad (III)$$

in which the radicals R2 to $R^4$ have the above meanings, are caused to react in the presence of a base, said reaction being either a) carried out in the presence of a carboxylic acid derivative of the general formula IV $$R^5-\overset{O}{\overset{\|}{C}}-X, \qquad (IV)$$

in which the radical $R^5$ stands for hydrogen or an alkyl or aryl group and X is a halogen, alkoxy, or carboxylalkyl radical, or b) continued in the presence of a carboxylic acid derivative of the formula IV, and the amide of the formula I is isolated.

According to the invention, an amide of the formula II is converted. The radical $R^1$ can stand for hydrogen, as is preferred, or for an aliphatic radical such as an alkyl group, for example $C_1$–$C_6$ alkyl, or an alkenyl group, eg, $C_2$–$C_6$ alkenyl. Furthermore $R^1$ can stand for a cycloaliphatic radical such as $C_4$–$C_7$ cycloalkyl or for an aromatic radical such as $C_6$–$C_{10}$ aryl. All of these groups, and particularly the aromatic groups, can carry substituents which are inert under the reaction conditions, such as halogen, nitro, alkoxy, and alkyl. Examples of suitable compounds of the formula II are formamide, acetamide, propionamide, crotonamide, acrylamide, and benzamide.

An amide of the formula II is caused to react with a carbonyl compound of the formula III. The radicals $R^2$, $R^3$, and $R^4$ can stand for the groups mentioned above with reference to the radical $R^1$.

Examples thereof are acetaldehyde, propionaldehyde, benzaldehyde, acrolein, crotonaldehyde, acetone, diethyl ketone, 1-butanone, acetophenone, and methyl vinyl ketone, of which acetaldehyde and acetone are preferred.

The amount of carbonyl compound used in relation to the amide employed can vary within wide limits. Usually 0.5–10 equivalents, preferably 0.8–1.2 equivalents, of carbonyl compound are caused to react with one equivalent of amide.

The starting compounds of the formulas II and III are caused to react in the presence of a base, preferably a Brönsted base. Both inorganic and organic bases are suitable. Specific examples thereof are carbonates and hydrogen carbonates of alkali metals and alkaline earth metals such as sodium carbonate, potassium carbonate, and sodium hydrogen carbonate, quaternary ammonium carbonates such as tetramethylammonium carbonate, amides such as alkali metal amides, eg, sodium amide and potassium amide, hydroxides such as alkali metal hydroxides, eg, lithium hydroxide, sodium hydroxide, and potassium hydroxide, alkali metal carboxylates such as sodium acetate, alcoholates such as alkali metal alcoholares, eg, sodium methanolate, sodium ethanolate, potassium methanolate, and potassium tert-butanolate. Potassium hydroxide can also be used together with crown ethers such as 18-crown-6.

Other examples of suitable bases are amines such as ammonia as well as primary, secondary, and tertiary amines, of which the tertiary amines are preferred. The amines, can carry aliphatic, cycloaliphatic, or aromatic radicals, for example, trialkylamines such as trioctylamine, ethyldiisopropylamine, diethylisopropylamine, dimethylcyclohexylamine, triethylamine and also cyclic amines such as 2,2,6,6-tetramethylpiperidine, 1,4-diazabicyclo[2.2.2] octane, 1,8-diazabicyclo[5.4.0:]un-dec-7-ene, 1,5-diazabicyclo[4.3.0] non-5-ene, amines carrying aliphatic and aromatic radicals such as 1,8-bis (dimethylamino)naphthalene and 4-dimethylaminopyridine and heterocyclic amines such as N-alkylimidazoles and N-arylimidazoles, eg, N-methylimidazole and N-butylimidazole. Furthermore, amides such as dialkyl carboxamides, eg. dibutyl formamide are suitable. The process of the invention can be carried out, if desired, in the presence of basic ion exchangers which usually consist of sulfonated poly(styrene-co-divinyl benzene)s such as Amberlite®, Lewatit®, and Puralit®, and in the presence of basic zeolites such as hydrotalcite.

Furthermore, the starting compounds of the formulas II and III are caused to react with a carboxylic acid derivative of the formula IV. This carries a radical $R^5$ which stands for an alkyl group, preferably $C_1$–$C_6$ alkyl, or an aryl group such as $C_6$–$C_{10}$ aryl, eg. phenyl, or for hydrogen. The variable X denotes halogen such as chlorine or bromine, carboxyalkyl, preferably carboxy($C_1$–$C_4$ alkyl), or preferably an alkoxy radical, particularly $C_1$–$C_4$ alkoxy such as ethoxy. The use of esters as carboxylic acid derivate of the formula IV is preferred over the use of carboxylic halides or carboxylic anhydrides, since no acids capable of neutralizing the base employed are formed in this case as by-product.

Examples of suitable compounds are methyl formate, ethyl formate, methyl acetate, ethyl acetate, methyl propionate, and ethyl propionate, in addition to acetanhydride, propionic anhydride, and acetyl chloride.

The amount of the carboxylic acid derivatives of the formula IV employed is generally 0.5–10 equivalents, preferably 0.8–1.2 equivalents per equivalent of amide of the formula II.

The amount of base is usually approximately 0.1–5 equivalents per equivalent of amide of the formula II. If carboxylic acid esters of the formula IV are used, 0.5–1.5 equivalents of base are preferred, whilst in the case of the carboxylic acid halides and carboxylic acid anhydrides 1.5–2.5 equivalents of base are used.

Although the reaction is preferably carried out without the use of solvent, a solvent can be added however, eg, an aprotic solvent such as an ether, eg. tetrahydrofuran, an aromatic hydrocarbon such as toluene or xylene, and also acetonitrile, hexamethylphosphoric acid triamide, sulfolane, and dimethyl sulfoxide. The amount thereof is generally approximately 10–90 wt %, based on the total batch.

The temperature of reaction is generally approximately 0°–150° C., preferably 20°–100° C. and more preferably 30°–80° C. The process can usually be carried out under standard pressure conditions. If readily volatile starting compounds are used, however, it has been found to be advantageous to carry out the reaction under the resulting autogenous pressures of the reaction mixtures.

The process of the invention can be carried out continuously or batchwise. Suitable reactors are tubular reactors as well as stirred boilers.

In the preferred variant a), the reaction is carried out as a single-stage reaction. The starting compounds of the formulas II, III and IV and the base are mixed and brought to the temperature of reaction. The order of addition of the starting compounds is unimportant. It has been found to be advantageous to start with the base and the amide of the formula II and to add thereto a mixture of the carbonyl compound of the formula III and the carboxylic acid derivative of the formula IV or the individual components.

In the process variant b), the amide of the formula I and the carbonyl compound of the formula IV are first of all caused to react under the prescribed reaction conditions (monitoring of the reaction can take place by gas chromatography) and the resulting reaction mixture is then caused to react further with the carboxylic acid derivative of the formula IV.

The entire reaction is usually complete following a period of 1–12 h.

The reaction mixture thus obtained can be worked up in known manner. The product is generally separated by distillation. To the bottoms in the distilling apparatus there can be added strong bases such as caustic soda solutions to effect liberation of the organic bases from the salts formed during the reaction. The liberated bases can then be isolated by extraction or by distillation. If, in the reaction of the invention, readily volatile salt-like compounds such as formates of tertiary ammonium compounds are formed, these can be purified by distillation and converted to the corresponding amines, if desired. The bases separated in each case can be recycled to the reaction.

The process of the invention allows for the preparation, in a simple manner, from a process engineering point of view, of N-alkenyl carboxamides from readily available precursors. The reaction proceeds at mild temperatures of reaction and leads to a high yield of the end products. The process allows for the preparation of a large number of variously substituted N-alkenyl carboxamides.

EXAMPLES

Example 1

A mixture of 30 g (0.5 mol) of methyl formate and 22 g (0.5 mol) of acetaldehyde was added dropwise over a period of 20 min to a mixture of 22.5 g (0.5 mol of formamide and 50.5 g of triethylamine at room temperature. Heating at 40° C. was then continued for 3.5 h. There were obtained, by distillation, 27 g (76% of theory) of vinyl formamide in addition to 1.3 g of formamide. Excess triethylamine was recovered.

Example 2

In a manner similar to that described in Example 1, a mixture of 22.5 g (0.5 mol) of formamide and 50.5 g of triethylamine was first of all caused to react at 10° C. with 22 g (0.5 mol) of acetaldehyde and then, at room temperature, with 30 g (0.5 of methyl formate. There were obtained 25.8 g (72.7% of theory) of vinylformamide.

Example 3

In a manner similar to that described in Example 1,22.5 g (0.5 mol) of formamide, 30 g (0.5 mol) of methyl formate, and 22 g (0.5 mol) of acetaldehyde were caused to react at 35° C. in the presence of 53 g (0.5 mol) of $Na_2CO_3$. Yield 69%.

Example 4

In a manner similar to that described in Example 1 there was obtained N-propenyl formamide, in a yield of 76%, from 22.5 g (0.5 mol) of formamide, 50.5 g of triethylamine, 30 g (0.5 mol of methyl formate and 29 g (0.5 mol) of propanol.

Example 5

In a manner similar to that described in Example 1, 126 g (87% of theory) of N-vinyl benzamide were obtained from 119 g (1 mol) of benzamide, 110 g (1.09 mol) of triethylamine, 95 g (1.09 mol) of methyl formate and 44 g (1 mol) of acetaldehyde.

Example 6

In a manner similar to that described in Example 1, 59 g (1 too1) of acetamide, 110 g (1.09 mol) of triethylamine, 44 g of acetaldehyde and 94 g (1.09mol) of vinyl acetate were caused to react at 50° C. Yield 76.6 g (90 % of theory).

We claim:

1. A process for the preparation of an N-alkenyl carboxamide of the general formula I $$R^1-C(=O)-NH-CR^2=CR^3R^4, \quad (I)$$

in which the radicals $R^1$ to $R^4$ independently stand for hydrogen or for aliphatic, cycloaliphatic, or aromatic radicals, which optionally carry inert substituents, wherein an amide of the general formula $$R^1-C(=O)-NH_2, \quad (II)$$

in which the radical $R^1$ has the above meaning, and a carbonyl compound of the general formula III $$R^2-C(=O)-CHR^3R^4, \quad (III)$$

in which the radicals $R^2$ to $R^4$ have the above meanings, are caused to react in the presence of a base, said reaction being either a) carried out in the presence of a carboxylic acid derivative of the general formula IV $$R^5-C(=O)-X, \quad (IV)$$

in which the radical $R^5$ stands for hydrogen or an alkyl or aryl group and X is a halogen, alkoxy, or carboxylalkyl radical, or b) continued in the presence of a carboxylic acid derivative of the formula and the amide of the formula I is isolated.

2. A process as defined in claim 1, wherein the radicals $R^2$ to $R^4$ stand for hydrogen.

3. A process as defined in claim 1, wherein the carboxylic acid derivative of the formula IV used is an alkyl formate.

4. A process as defined in any of claim 1, wherein N-vinyl formamide is synthesized.

5. A process as defined in any of claim 1, wherein the base used is a tertiary amine.

6. A process as defined in claim 1, wherein the reaction is carried out at 30°–80° C.

* * * * *

UNITED STATES PATENT AND TRADEMARK OFFICE
CERTIFICATE OF CORRECTION

PATENT NO.: 5,710,331

DATED: January 20, 1998

INVENTOR(S): HEIDER et al.

It is certified that error appears in the above-identified patent and that said Letters Patent is hereby corrected as shown below:

Column 6, claim 1, line 10, insert --IV-- after "formula".

Signed and Sealed this

Twenty-first Day of April, 1998

Attest:

BRUCE LEHMAN

Attesting Officer  Commissioner of Patents and Trademarks